United States Patent
Wedan et al.

(10) Patent No.: US 7,610,101 B2
(45) Date of Patent: Oct. 27, 2009

(54) RF REJECTING LEAD

(75) Inventors: Steven R. Wedan, Savage, MN (US); Thomas W. Lloyd, Spring Lake Park, MN (US); Kevin J. Ely, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 321 days.

(21) Appl. No.: 11/565,219

(22) Filed: Nov. 30, 2006

(65) Prior Publication Data
US 2008/0132985 A1 Jun. 5, 2008

(51) Int. Cl.
*A61N 1/00* (2006.01)
(52) U.S. Cl. ...................................................... 607/116
(58) Field of Classification Search ................. 607/116
See application file for complete search history.

(56) References Cited

U.S. PATENT DOCUMENTS

| | | | |
|---|---|---|---|
| 3,614,692 A * | 10/1971 | Rozelle et al. ................. 336/15 |
| 6,993,373 B2 | 1/2006 | Vrijheid et al. | |
| 7,013,180 B2 | 3/2006 | Villaseca et al. | |
| 7,363,090 B2 * | 4/2008 | Halperin et al. ............. 607/116 |
| 2003/0144720 A1 | 7/2003 | Villaseca et al. | |
| 2003/0144721 A1 | 7/2003 | Villaseca et al. | |
| 2004/0122490 A1 * | 6/2004 | Reinke et al. ................. 607/60 |
| 2005/0090886 A1 | 4/2005 | MacDonald et al. | |
| 2005/0222658 A1 | 10/2005 | Hoegh et al. | |
| 2006/0009819 A1 | 1/2006 | Przybyszewski | |
| 2006/0041294 A1 | 2/2006 | Gray | |
| 2006/0229693 A1 * | 10/2006 | Bauer et al. ................. 607/116 |
| 2008/0049376 A1 * | 2/2008 | Stevenson et al. ........... 361/302 |

\* cited by examiner

*Primary Examiner*—George Manuel
*Assistant Examiner*—Robert N Wieland
(74) *Attorney, Agent, or Firm*—Faegre & Benson LLP (57) ABSTRACT

A lead assembly for an implantable medical device. The lead assembly comprises a lead body having a first portion and a second portion. The first portion is adapted for coupling to a pulse generator and the second portion is adapted for implantation in or near a heart. First and second co-radial conductive coils are positioned within the lead body and electrically isolated from each other. The first and second conductive coils include a first and second number of coil turns and the first number is substantially equivalent to the second number. A ring electrode is located at the second portion and a tip electrode is located distal to the ring electrode and coupled to the second conductive coil. The first conductive coil extends past the ring electrode and transitions to a non-coiled region, which extends back to and couples to the ring electrode.

19 Claims, 6 Drawing Sheets

RF REJECTING LEAD

TECHNICAL FIELD

The present invention relates to implantable medical devices. The present invention relates more particularly to a method and apparatus for reducing the effects of electromagnetic fields applied to medical devices including a pulse generator and a lead system.

BACKGROUND

Patients who have been implanted with a medical device including a pulse generator and a lead system, such as a cardiac pacemaker or a defibrillator, are sometimes subjected to electromagnetic energy. A magnetic resonance imaging (MRI) procedure is one example of a procedure where a patient is subjected to electromagnetic energy. An MRI uses a powerful magnetic field, radiofrequency (RF) waves, and a rapidly changing magnetic field to demonstrate whether or not there is an injury or some disease process present. MRI is an efficient technique used in the diagnosis of many disorders, including neurological and cardiac abnormalities and other diseases. MRI has achieved prominence in both the research and clinical arenas. It provides a non-invasive method for examining internal body structures and functions. Because MRI has become such a useful diagnostic tool, it now is used extensively in hospitals and clinics around the world.

One problem associated with MRI scanning of a patient having a pulse generator and lead system is that the RF excitation output from the MRI scanner can be coupled into a lead conductor and then delivered as current out of the lead at the interface between a lead electrode and body tissue. The current density at the lead electrode can be sufficient to cause appreciable current loss in the body tissue, resulting in heat generation. This RF-induced heating may cause tissue damage at the electrode/tissue interface, as well as negatively affect performance of the medical device.

One method of reducing RF-induced heating at an electrode/tissue interface is the inclusion of an RF choke component near the electrode, generally at a distal end of the lead. Such RF choke components are typically insulated coils having inductive and capacitive effects that reduce the flow of current. The RF choke component thus acts as an electromagnetic filter and/or trap that blocks RF excitation currents from flowing through the electrode. Another method of reducing RF-induced heating at an electrode/tissue interface is shielding the lead conductor from RF energy.

Current devices and methods for reducing RF-induced heating in pulse generator and lead systems require additional lead components or materials, and therefore increase the cost and bulk of the lead system. Thus, there is a need in the art for an RF choke assembly that minimizes the number of additional components and materials. There is a further need in the art for an RF choke assembly that does not significantly increase the cost and bulk of the lead system.

SUMMARY

In one embodiment, the invention is a lead assembly for an implantable medical device. The lead assembly comprises a lead body having a first portion and a second portion. The first portion is adapted for coupling to a pulse generator and the second portion is adapted for implantation in or near a heart. First and second co-radial conductive coils are positioned within the lead body and electrically isolated from each other. The first and second conductive coils include a first and second number of coil turns and the first number is substantially equivalent to the second number. A ring electrode is located at the second portion and a tip electrode is located distal to the ring electrode and coupled to the second conductive coil. The first conductive coil extends past the ring electrode and transitions to a non-coiled region, which extends back to and couples to the ring electrode.

In one embodiment, the invention is a lead assembly for an implantable medical device. The lead assembly comprises a lead body having a first portion and a second portion. The first portion is adapted for coupling to a pulse generator and the second portion is adapted for implantation in or near a heart. First and second electrodes are located at the second portion. A first means for blocking RF currents is coupled to the first and second electrodes.

In one embodiment, the invention is a lead assembly for an implantable medical device. The lead assembly comprises a lead body having a first portion and a second portion. The first portion is adapted for coupling to a pulse generator and the second portion is adapted for implantation in or near a heart. First and second co-radial conductive coils are positioned within the lead body and electrically isolated from each other. The first and second conductive coils include a first and second number of coil turns. The first and second number of coil turns include a number of matched turns and a number of unmatched turns, and the number of unmatched turns divided by the total of unmatched and matched turns is less than approximately 1.5%. A first electrode located at the second portion and coupled to the first conductive coil and a second electrode is located at the second portion and coupled to the second conductive coil.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
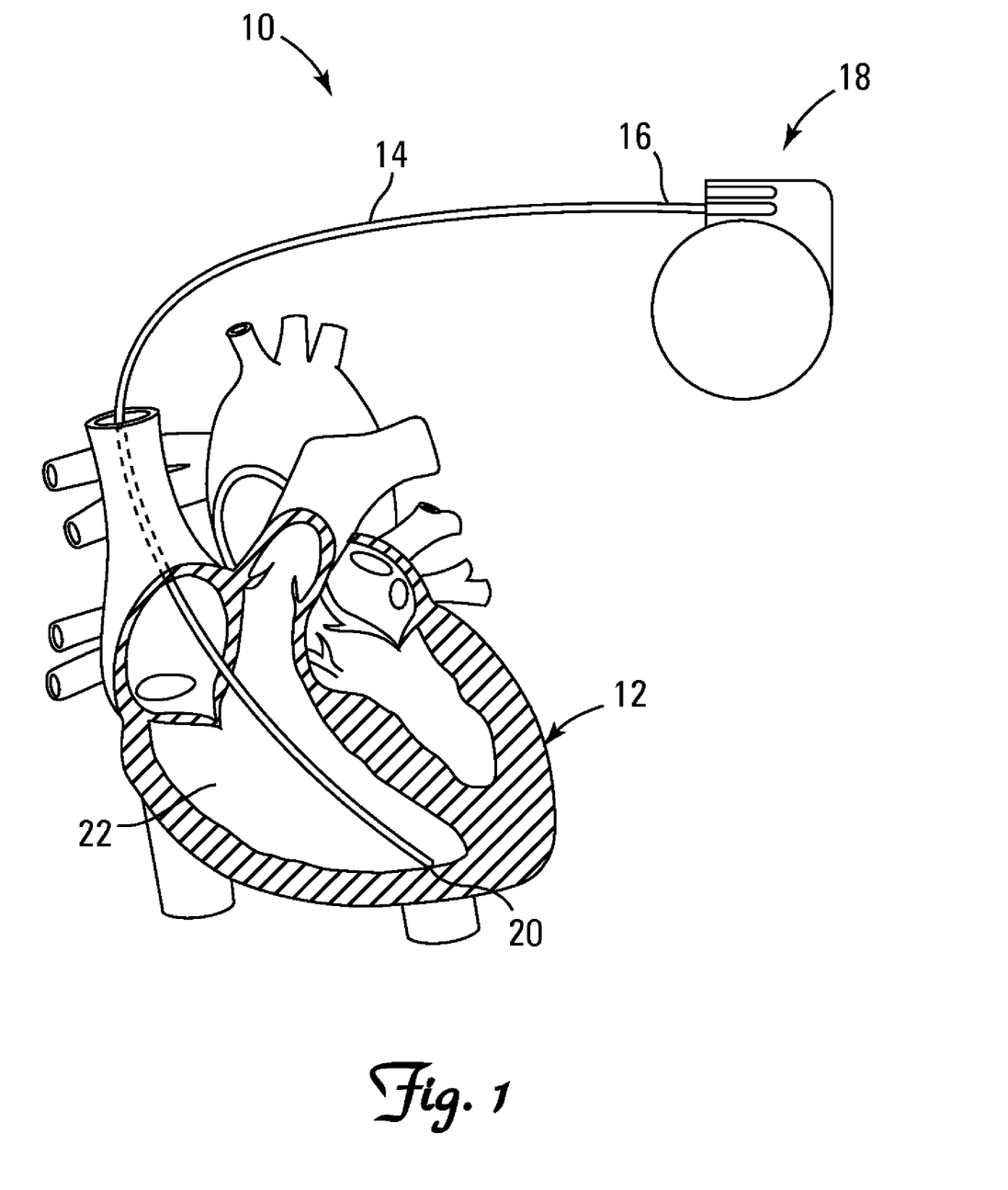
FIG. 1 shows an exemplary implantable medical device in relation to a heart that can be used with embodiments of the present invention.

FIG. 1 shows an exemplary implantable medical device 10 in relation to a heart 12 that can be used with embodiments of the present invention. The implantable medical device 10 includes a lead assembly 14 extending from a first portion 16 coupled to a pulse generator 18 to a second portion 20 implanted in the heart 12. The implantable medical device 10 may be, for example, a pacemaker, defibrillator, or similar type of device. Furthermore, while the second portion 20 of the lead assembly 14 is shown implanted in a right ventricle 22 of the heart 12, the second portion 20 of the lead assembly 14 can be implanted anywhere in or near the heart 12, as is known in the art of cardiac rhythm management.

Figure 2:
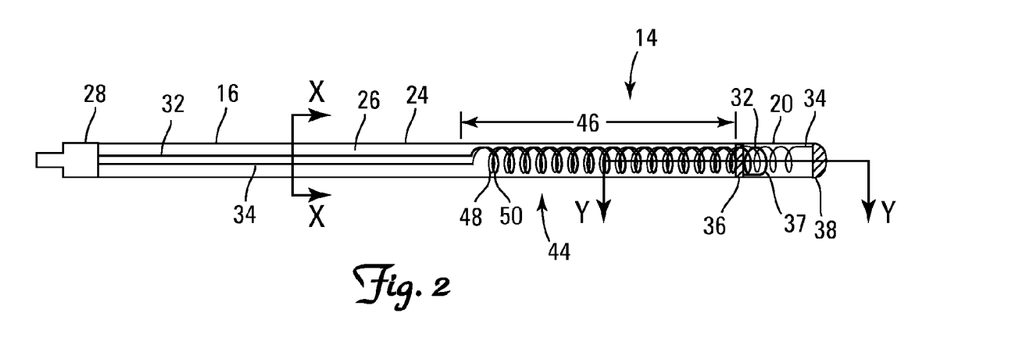
FIG. 2 shows a side schematic view of the lead assembly of FIG. 1 according to one embodiment of the present invention.

FIG. 2 is a schematic representation of the lead assembly 14 and is not intended to illustrate its dimensions. The lead assembly 14 includes an elongated lead body 24 defining a lumen 26 extending from the first portion 16 to the second portion 20. A connector 28 for connecting the lead assembly 14 to the pulse generator 18 is located on the first portion 16. First and second conductive members 32, 34 extend through the lumen 26. Electrodes 36, 38 are located on the second portion 20 and are electrically coupled to the first and second conductive members 32, 34. In the illustrated embodiment, the first electrode 36 is a ring electrode and the second electrode 38 is a tip electrode. However, the electrodes 36, 38 can be any type of electrode known in the art of cardiac leads.

Figure 3:
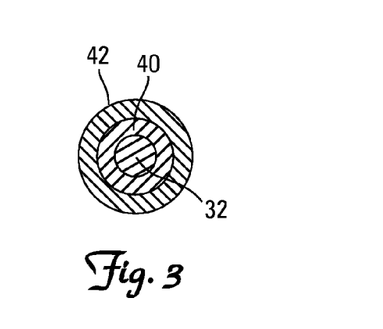
FIG. 3 shows a sectional view of the first conductive member of the lead assembly of FIG. 2 taken along line X-X.

The first and second conductive members 32, 34 are insulated from one another. Both the first and second conductive members 32, 34 have an insulative or non-conductive coating 40. FIG. 3 illustrates the first conductive member 32 in more detail, and shows the non-conductive coating 40. The insulative coating 40 may be formed of a silicone material, Teflon, expanded tetrafluoroethylene (eTFE), polytetrafluoroethylene (pTFE) or another suitable non-conductive material. In other embodiments, only one of the conductive members 32, 34 has the insulative coating 40.

The lead assembly 14 may further include a grounded electromagnetic shield 42 over one or both of the first and second conductive members 32, 34. The shield 42 may be formed of gold or other materials as are known in the art. Optionally, the shield 42 may be formed over the elongated body 24 (not shown). In other embodiments, the shield 42 is not present.

Figure 4:
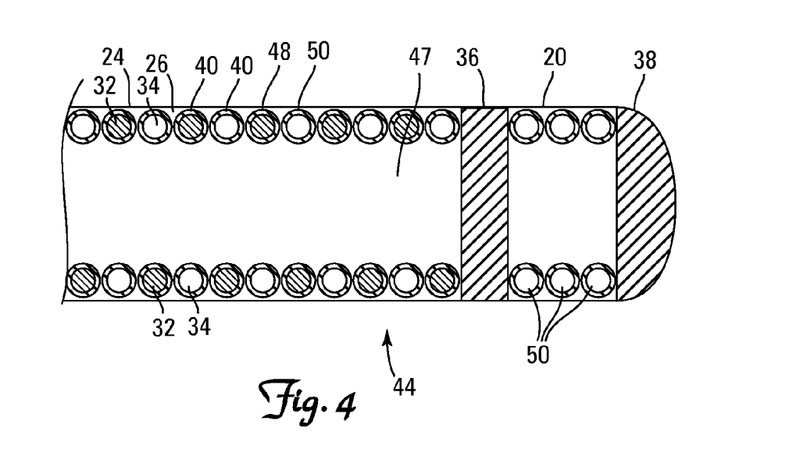
FIG. 4 shows a detailed sectional view of the choke assembly portion of the lead assembly of FIG. 2 taken along line Y-Y.

The lead assembly 14 further includes a choke assembly 44 located within the lumen 26 (shown in FIG. 2). In other embodiments, the choke assembly 44 can be embedded within the lead body 24. The choke assembly 44 includes a co-radial coiled region 46 where the conductive members 32, 34 are wound in the same direction and the coils have the same diameter. FIG. 4 shows a portion of the choke assembly 44 according to one embodiment of the invention. As illustrated in FIG. 4, the conductive members 32, 34 define a single lumen 47 which is centrally located with respect to both conductive members 32, 34. When the lead assembly 14 is subjected to an RF field, as during an MRI scan, the co-radial coiled region 46 blocks common mode AC signals from traveling along the conductive members 32, 34. RF-induced currents of opposite polarities are formed in each of the conductive members 32, 34 at the co-radial coiled region 46. The RF-induced currents cancel one another out, thereby blocking RF-induced currents from exiting through the electrodes 36, 38.

The conductive members 32, 34 each form a plurality of coil turns 48, 50, respectively, at the choke assembly 40. The effectiveness of the choke assembly 44 is increased when the first and second conductive members 32, 34 have an equal number of coil turns 48, 50. When the number of turns 48, 50 is not equal, the difference in the number of turns 48, 50 can be approximated by calculating an unmatched turns percentage $t_p$. As shown in the equation below, the unmatched turns percentage $t_p$ is calculated by dividing the number of unmatched turns $t_{unmatched}$ by the total of the number of unmatched turns $t_{unmatched}$ plus the number of matched turns $t_{matched}$, then multiplying by 100.

$$t_p = \frac{t_{unmatched}}{t_{unmatched} + t_{matched}} \cdot 100$$

For example, a co-radial coiled region 46 having two extra turns 50 and ninety-eight matched turns 48, 50 would have an unmatched turns percentage of two (2%). This unmatched turns percentage correlates to the amount of RF leakage through the lead assembly 14 and out the electrode 38. The number of coil turns 48, 50 is substantially equivalent when the RF leakage is minimized, thereby reducing the level of tissue damage resulting from subjecting the lead assembly 14 to the RF field to an acceptable level. One of skill in the art can determine the level of RF leakage based on factors such as the wire used for the conductive members 32, 34, the dimensions of the electrode 38, and the length of the lead assembly 14.

Thus, in one embodiment of the invention, the first conductive member 32 has a substantially equivalent number of turns 48 as the second conductive member 34 has turns 50. In one embodiment of the invention, the unmatched turns percentage is less than approximately 2.0. In one embodiment, the unmatched turns percentage is less than approximately 1.6. In one embodiment, the unmatched turns percentage is less than approximately 1.5. In an alternative embodiment, the unmatched turns percentage is less than approximately 1.0. In yet another alternative embodiment, the unmatched turns percentage is less than approximately 0.5. In another alternative embodiment, the unmatched turns percentage is less than approximately 0.3. In yet another alternative embodiment, the unmatched turns percentage is less than approximately 0.2. In one embodiment, the unmatched turns percentage is 0 (i.e. the number of turns 48, 50 is the same).

In the embodiment illustrated in FIG. 4, the length of the second conductive member 34, and thus the number of coil turns 50, is slightly greater than the length and number of turns 48 of the first conductive member 32. This difference in the number of coil turns 48, 50 can occur because the first and second electrodes 36, 38 are not located at the same position along the lead body 24. As shown in FIG. 2, the number of turns 50 is greater than the number of turns 48 because the conductive member 34 extends past the electrode 36 to the electrode 38. In the embodiment illustrated in FIG. 2, the first conductive coil 32 extends past the ring electrode 36 and transitions to a non-coiled region 37, which extends back and electrically couples to the ring electrode 36. In the illustrated embodiment, the turns 48 of the conductive member 32 extend approximately halfway between the electrodes 36, 38. In other embodiments, the turns 48 can extend a lesser or greater distance beyond the electrode 36 before returning to the electrode 36. In one embodiment, the turns 48 extend between approximately one-quarter and three-quarters of the distance between the electrodes 36, 38.

In the embodiment illustrated in FIG. 2, the co-radial coiled region 46 extends along only a portion of the lead body 24. In other embodiments (not shown), the co-radial conductive region 46 extends substantially along the entire length of the lead body 24 (i.e., from the first portion 16 to the second portion 20). In other embodiments, the length of the co-radial coiled region 46 and the number of coil turns 48, 50 can be selected to block or filter wavelengths having a particular frequency. For example, the length of the co-radial coiled region 46 and the number of turns 48, 50 can be selected so that the length of the co-radial coiled region 46 is less than one-quarter of the operating wavelength of an MRI machine. In one embodiment, the length and number of turns 48, 50 in the co-radial coiled region 46 can block frequencies generated by a 1.5 Tesla system (operating frequency 63 Mega-Hertz). In another embodiment, the length and number of turns 48, 50 of the co-radial coiled region 46 can block frequencies generated by a 3T system (operating frequency 128 MHz). The length of the co-radial region 46 and number of turns 48, 50 varies based on design parameters. These design parameters include the tightness of the winding of the turns 48, 50, the type of wire and diameter of the wires used for the conductive members 32, 34, the thickness of the insulative coating 40, and the capacitance of the conductive members 32, 34. In one embodiment, the distance between turns 48, 50 is approximately zero.

Figure 5:
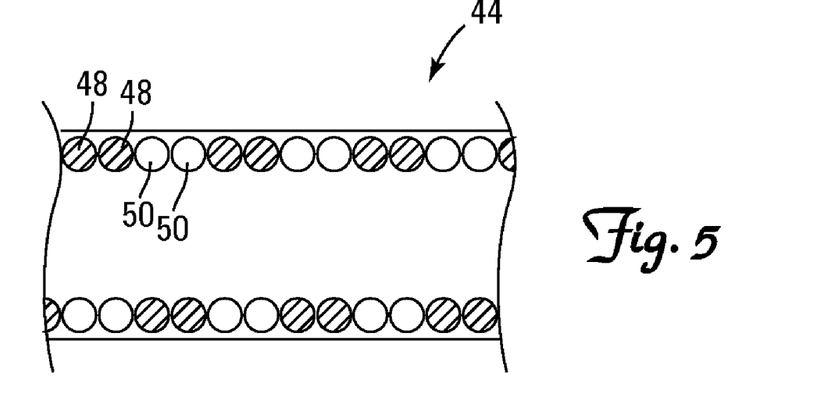
FIG. 5 shows a sectional view of a portion of a choke assembly according to another embodiment of the present invention.
Figure 6:
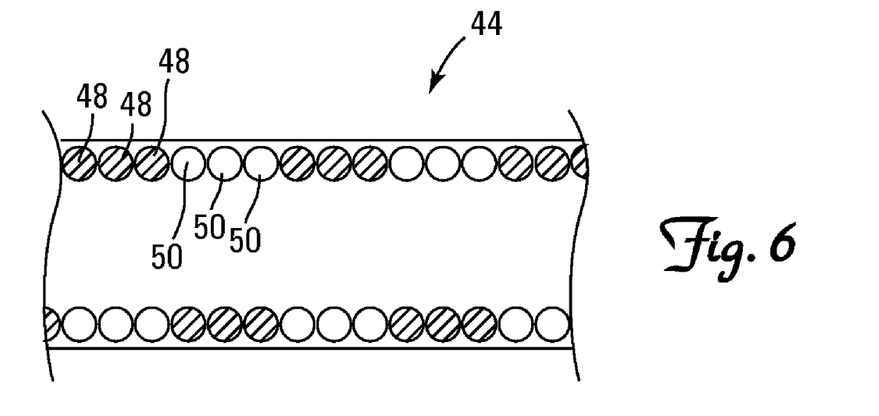
FIG. 6 shows a sectional view of a portion of a choke assembly according to another embodiment of the present invention.
Figure 7:
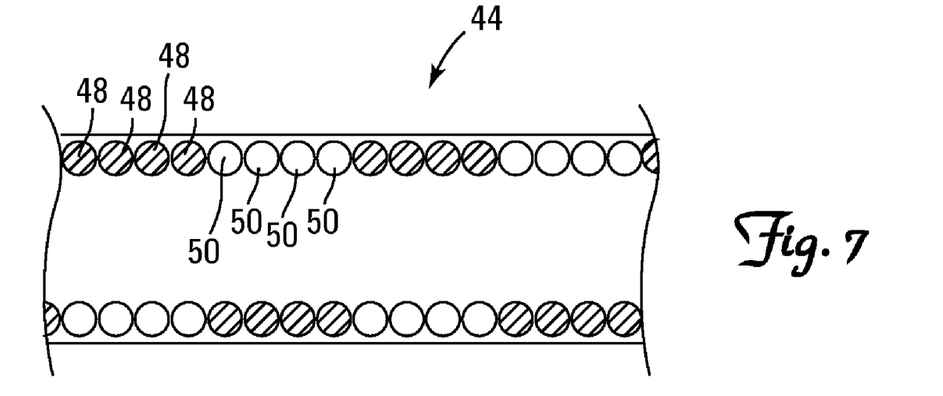
FIG. 7 shows a sectional view of a portion of a choke assembly according to another embodiment of the present invention.

In the embodiment illustrated in FIG. 4, the turns 48, 50 are offset from one another on a one to one basis. FIGS. 5-7 illustrate additional embodiments of the choke assembly 44 where the turns 48, 50 of the first and second conductive members 32, 34 are offset from one another on a two to two (FIG. 5), three to three (FIG. 6) or four to four (FIG. 7) basis. In other embodiments (not shown), the turns 48, 50 of the first and second conductive members 32, 34 may be offset on a two to three basis, or on any other basis where the first conductive member 32 has substantially the same number of turns 48 as the second conductive member 34 has of turns 50.

Figure 8:
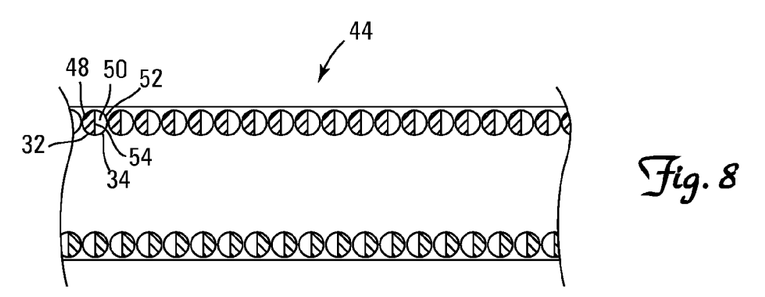
FIG. 8 shows a sectional view of a choke assembly according to another embodiment of the present invention.
Figure 9:
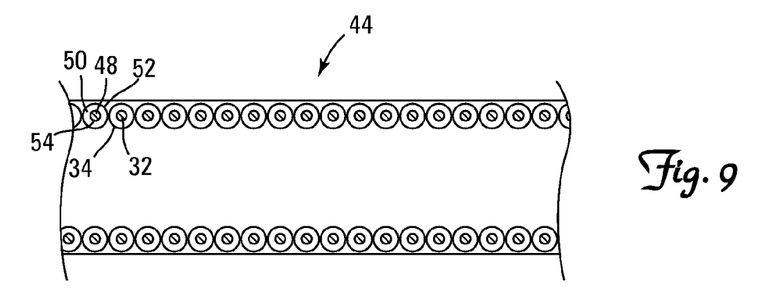
FIG. 9 shows a sectional view of a choke assembly according to another embodiment of the present invention.

FIGS. 8 and 9 illustrate additional embodiments of the invention where the first and second conductive members 32, 34 are formed on a unitary conductive member 52. In the embodiment illustrated in FIG. 8, the first and second conductive members 32, 34 are halves of the unitary conductive member 52. An insulative barrier 54 insulates the first and second conductive members 32, 34 from each other. In the alternative embodiment illustrated in FIG. 9, the second conductive member 34 is formed about the first conductive member 32 such that the first and second conductive members 32, 34 are co-axial as well as co-radial. The insulative barrier 54 is formed about the first conductive member 32 so that the conductive members 32, 34 are electrically isolated from one another. The unitary conductive member 52 can optionally be surrounded by an insulative coating (not shown).

Figure 10:
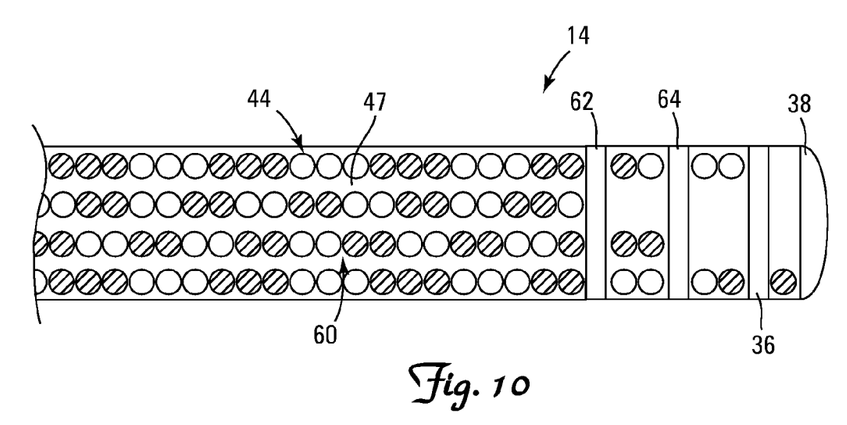
FIG. 10 shows a sectional view of a choke assembly according to another embodiment of the present invention.

FIG. 10 shows a portion of a lead assembly according to another embodiment of the invention. In this embodiment, a second choke assembly 60 is positioned in the lumen 47 defined by the first choke assembly 44. The second choke assembly 60 is in all respects similar to the first choke assembly 44, and provides RF choke capabilities for a third and a fourth electrode 62, 64 on the lead assembly 14. Alternatively, the second choke assembly 60 could comprise any other choke assembly known in the art.

Figure 11:
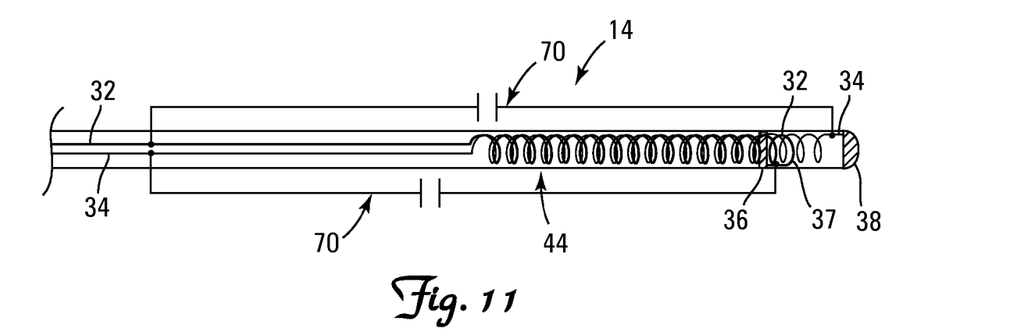
FIG. 11 shows a schematic view of a choke assembly according to another embodiment of the present invention.
Figure 12:
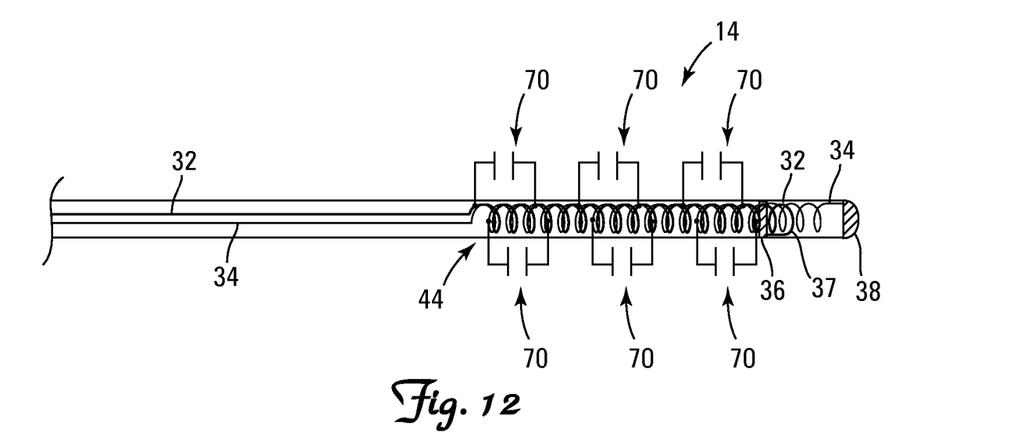
FIG. 12 shows a schematic view of a choke assembly according to another embodiment of the present invention.

FIGS. 11 and 12 are schematics illustrating additional embodiments of the choke assembly 44 where the choke assembly 44 further includes a capacitor element 70 for blocking. In the embodiment shown in FIG. 11, the lead assembly 14 includes a capacitor 70 connected in parallel with the conductive member 32 and an additional capacitor 70 connected in parallel with the conductive member 34. When the capacitors 70 are connected as illustrated in FIG. 11, they broaden the blocked frequency range of the choke assembly 44, thereby reducing the quality factor Q of the choke assembly 44. In the illustrated embodiment, the capacitor elements 70 extend the length of the lead assembly 14. FIG. 12 illustrates another embodiment where the choke assembly 44 has a plurality of capacitor elements 70. In the illustrated embodiment, three capacitors 70 are connected in parallel with the conductive member 32 and three capacitors 70 are connected in parallel with the conductive member 34. The embodiment of FIG. 12 simulates the performance of the embodiment of FIG. 11. In an alternative embodiment, the choke assembly 44 could include four, eight, or any other number of capacitors 70.

Figure 13A:
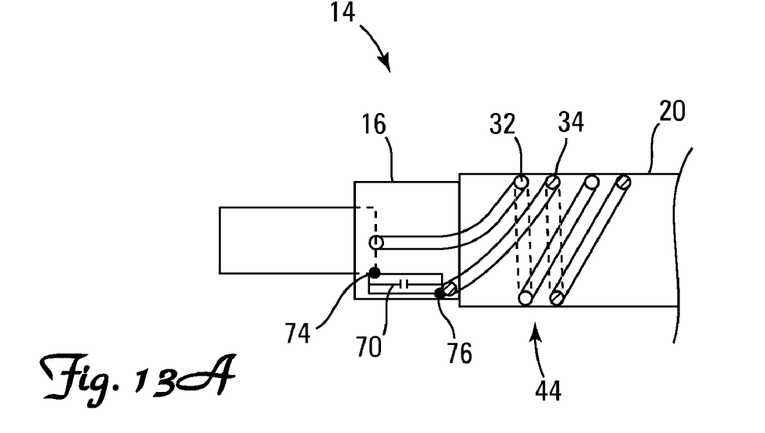
FIGS. 13A-13C show sectional views of a choke assembly according to another embodiment of the present invention.
Figure 13B:
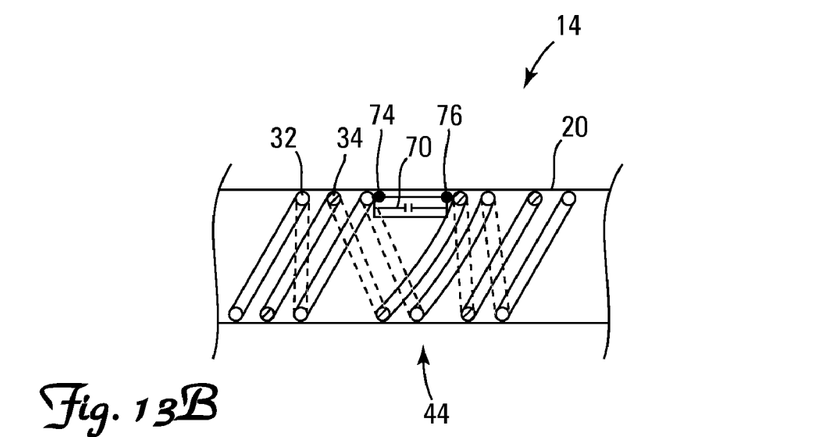
Figure 13C:
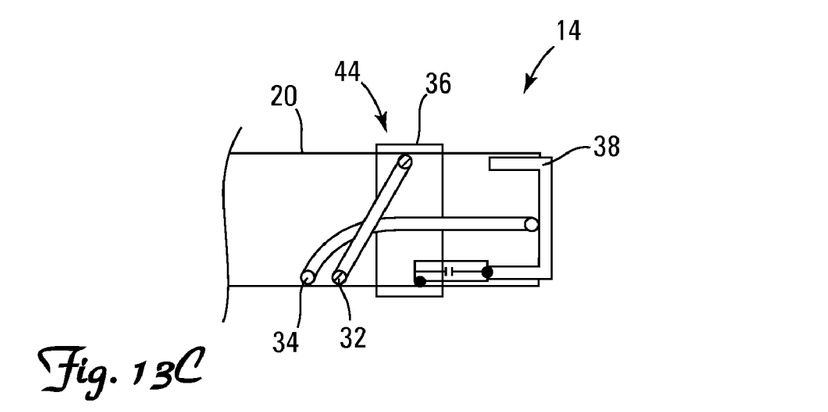

FIGS. 13A-13C illustrate alternative embodiments of the choke assembly 44 where the capacitor element 70 is connected between the conductive elements 32, 34. As shown in FIG. 13A, the capacitor element 70 is connected between connector pins 74, 76 and located in the first portion 16 of the lead assembly 14. The connector pins 74, 76 are connected to conductive elements 32, 34, respectively. When the capacitor element 70 is connected between the conductive elements 32, 34, it shorts out any excess RF-induced current carried by the conductive element 32 or 34, thus selectively reducing the amount of excess RF-induced current exiting out the electrodes 36, 38.

In the embodiment shown in FIG. 13B, the capacitor element 70 is located between the first end 16 and the second end 20, and is connected between the conductive elements 32, 34. The lead assembly 14 can include a rigid internal fixture (not shown) that can isolate the pins 74, 76 and capacitor assembly 70 from flexing and torsion of the lead assembly 14. FIG. 13C illustrates yet another embodiment of the choke assembly 44 where the capacitor element 70 is located at the second portion 20 of the lead assembly 14. As shown in FIG. 13C, the capacitor element 70 is coupled to the ring electrode 36 and the tip electrode 38. The embodiments shown in FIGS. 13B and 13C short out excess RF-induced current carried by conductive element 32 or 34 in the manner described with respect to FIG. 13A.

Although a single capacitor element 70 is shown in FIGS. 13A-13C, in other embodiments, the position and value of the capacitor elements 70 may vary as needed. For example, a lead assembly 14 can include capacitors 70 located at the first end 16, the second end 20, and between the first and second ends 16, 20. In yet another alternative embodiment, the lead assembly 14 can include a plurality of capacitors 70 located between the first and second ends 16, 20. In yet another alternative embodiment, the lead assembly 14 can include capacitors 70 connected between the conductive members 32, 34 and capacitors 70 connected in parallel with the conductive members 32, 34. In other embodiments, the lead assembly 14 can include a second choke assembly 60 or any combination of choke assemblies 44, 60 and capacitors 70.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A lead assembly for an implantable medical device, the lead assembly comprising:
    a lead body having a first portion and a second portion, the first portion adapted for coupling to a pulse generator and the second portion adapted for implantation in or near a heart;
    first and second co-radial conductive coils positioned within the lead body and electrically isolated from each other, wherein the first and second conductive coils include a first and second number of coil turns and the first number is substantially equivalent to the second number;
    a ring electrode located at the second portion; and
    a tip electrode located distal to the ring electrode and coupled to the second conductive coil;
    wherein the first conductive coil extends past the ring electrode to between the ring electrode and the tip electrode and transitions to a non-coiled region, which extends back to and couples to the ring electrode.

2. The lead assembly of claim 1 wherein the first conductive coil extends approximately halfway between the ring electrode and the tip electrode.

3. The lead assembly of claim 1 wherein the first conductive coil extends approximately one-quarter of the distance between the ring electrode and the tip electrode.

4. The lead assembly of claim 1 wherein the first conductive coil extends approximately three-quarters of the distance between the ring electrode and the tip electrode.

5. The lead assembly of claim 1 further comprising a first capacitor element connected in parallel with the first conductive coil and a second capacitor element connected in parallel with the second conductive coil.

6. The lead assembly of claim 1 further comprising a plurality of capacitor elements connected in parallel with the first conductive coil and a plurality of capacitor elements connected in parallel with the second conductive coil.

7. The lead assembly of claim 1 further comprising a capacitor element coupled between the first and second conductive coils.

8. The lead assembly of claim 1 further comprising a plurality of capacitor elements, each capacitor element coupled between the first and second conductive coils.

9. The lead assembly of claim 1 further comprising a first capacitor element connected in parallel with the first conductive coil, a second capacitor element connected in parallel with the second conductive coil, and a third capacitor coupled between the first and second conductive coils.

10. The lead assembly of claim 1 wherein the first and second conductive coils extend along a portion of the lead body.

11. The lead assembly of claim 1 wherein the lead body includes a lumen and the first and second conductive coils are located within the lumen.

12. The lead assembly of claim 1 wherein the first and second conductive coils are embedded within the lead body.

13. A lead assembly for an implantable medical device, the lead assembly comprising:
    a lead body having a first portion and a second portion, the first portion adapted for coupling to a pulse generator and the second portion adapted for implantation in or near a heart;
    first and second electrodes located at the second portion, wherein the second electrode is distal to the first electrode; and
    a first means for blocking RF currents coupled to the first and second electrodes, wherein the first means for blocking RF currents includes first and second co-radial conductive coils positioned within the lead body, wherein the second conductive coil is coupled to the second electrode, and wherein the first conductive coil extends past the first electrode to between the first electrode and the second electrode and transitions to a non-coiled region, which extends back to and couples to the first electrode.

14. The lead assembly of claim 13 wherein the first and second conductive coils are parts of a unitary conductive member.

15. The lead assembly of claim 14 wherein the second conductive coil is coaxial with the first conductive coil.

16. The lead assembly of claim 13 further comprising third and fourth electrodes located at the second portion and a second means for blocking RF currents coupled to the third and fourth electrodes.

17. A lead assembly for an implantable medical device, the lead assembly comprising:
    a lead body having a first portion and a second portion, the first portion adapted for coupling to a pulse generator and the second portion adapted for implantation in or near a heart;
    first and second co-radial conductive coils positioned within the lead body and electrically isolated from each other, wherein the first and second conductive coils include a first and second number of coil turns, the first and second number of coil turns include a number of matched turns and a number of unmatched turns, and the number of unmatched turns divided by the total number of unmatched and matched turns is less than approximately 1.5%;
    a first electrode located at the second portion and coupled to the first conductive coil; and
    a second electrode located at the second portion and coupled to the second conductive coil,
    wherein the first conductive coil extends past the first electrode to between the first electrode and the second electrode and transitions to a non-coiled region, which extends back to and couples to the first electrode.

18. The lead assembly of claim 17 wherein the number of unmatched turns divided by the total number of unmatched and matched turns is less than approximately 0.2%.

19. The lead assembly of claim 17 wherein the first and second conductive coils are offset on a one to one, two to two, three to three, two to three, three to two, or a four to four basis.

* * * * *